United States Patent [19]

White, Jr. et al.

[11] 4,137,402

[45] Jan. 30, 1979

[54] QUATERNARY AMMONIUM SALTS OF DANTROLENE AND CLODANOLENE

[75] Inventors: Ralph L. White, Jr.; George C. Wright, both of Norwich, N.Y.

[73] Assignee: Morton-Norwich Products, Inc., Norwich, N.Y.

[21] Appl. No.: 891,521

[22] Filed: Mar. 30, 1978

[51] Int. Cl.² ............... C07D 405/14; C07D 405/12
[52] U.S. Cl. .................................. 542/420; 542/432; 548/308; 548/309
[58] Field of Search .................. 542/420; 548/308, 309

[56] References Cited

U.S. PATENT DOCUMENTS 3,843,636  10/1974  White, Jr. .................... 542/420

FOREIGN PATENT DOCUMENTS 50-82060  3/1975  Japan ......................... 542/420

Primary Examiner—Allen B. Curtis
Attorney, Agent, or Firm—Anthony J. Franze

[57] ABSTRACT

Certain quaternary ammonium salts of dantrolene and clodanolene are effective skeletal muscle relaxants.

8 Claims, No Drawings

QUATERNARY AMMONIUM SALTS OF DANTROLENE AND CLODANOLENE

This invention relates to chemical compounds and more particularly to quaternary ammonium salts of dantrolene (1-[[[5-(4-nitrophenyl)-2-furanyl]methylene]amino]-2,4,-imidazolidinedione) and clodanolene (1-[[[5-(3,4-dichlorophenyl)-2-furanyl]methylene]amino]-2,4-imidazolidinedione) of the formula:

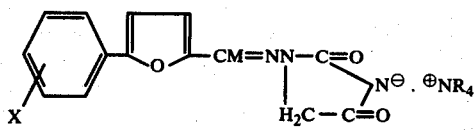

wherein X is 4-nitro or 3,4-dichloro and $^{\oplus}NR_4$ is N-methylpyridinium, 3,7-diamino-2,8-dimethyl-5-phenylphenazinium, 2,3-dimethyl-1-phenyl-4-trimethylammonium-3-pyrazoline-5-one, 1,3-dimethylimidazolium, choline, and 2-methyl-2-trimethylammonium-1-propanol.

These salts possess pharmacological activity. They are particularly noteworthy for the skeletal muscle relaxant effect elicited by them when administered to warm blooded animals. Upon intravenous administration to rats in a dose of about 3–8 mg/kg in tetrahydrofurfuryl alcohol a 50% inhibition of gastrochemius muscle twitch tension is secured.

The quaternary salts of this invention possess increased water solubility being from 10–50 times more soluble than the corresponding sodium salts of dantrolene and clodanolene.

The salts of this invention can be composed in a variety of pharmaceutical dosage forms such as tablets, solutions, elixirs, suspensions, capsules, and the like using adjuvants and excipients common to the pharmaceutical art and with which there is no incompatibility.

The method which is currently used in the preparation of the compounds of this invention consists in bringing together dantrolene or clodanolene and a quaternary ammonium hydroxide generated by passage of the corresponding quaternary ammonium halide through a basic ion exchange column in the presence of a solvent. A suitable basic ion exchange medium is Amberlite ® IRA-410 (Mallinckrodt).

In order that this invention may be readily available to and understood by those skilled in the art, the following illustrative examples for the preparation of the compounds are provided.

EXAMPLE I

1-[[[5-(4-Nitrophenyl)-2-furanyl]methylene]amino]-2,4-imidazolidinedione N-Methylpyridinium Salt Hydrate In a pressure bottle was placed pyridine (23 g, 0.29 mole), 1-propanol (100 ml), and the solution was cooled to 5°. Iodomethane (19 ml, 0.30 mole) was added, and the mixture was allowed to stand for seven days at ambient conditions. Filtration yielded 30 g of the quaternary salt.

N-Methylpyridinium iodide (22 g, 0.10 mole) dissolved in water (50 ml) was placed on a column of 250 l ml of Amberlite ® IRA-410 which had been previously rinsed with distilled water.

The salt was carried through the column with water (300 ml). Progress of the eluted quaternary hydroxide could either be followed by pH of eluate or by spotting a drop of eluate on a silica gel plate and examining the spot under UV light for a dark brown spot. The eluate was concentrated at room temperature to ca. 30 ml with a high vacuum pump. The solution was then diluted to 100 ml volume with methanol.

Dantrolene (19 g, 0.060 mole) was stirred in methanol (400 ml) while all the quaternary hydroxide solution was rapidly added. The solution was stirred for an hr., filtered, concentrated to 100 ml and allowed to crystallize. Filtration yielded brick-red product which was rinsed with isopropanol and air-dried to yield 21 g (83%), m.p. 148°–151° (dec). Two recrystallizations from nitromethane gave a hydrated sample of analytical purity, m.p. 173°–175°.

Anal. Calc'd. for $C_{20}H_{17}N_5O_5 \cdot \frac{3}{4} H_2O$: C, 57.07; H, 4.43; N, 16.64; $H_2O$, 3.21. Found: C, 56.98; H, 4.75; N, 16.64; $H_2O$, 3.49.

EXAMPLE II

1-{[5-(3,4-Dichlorophenyl)furfurylidene]amino}hydantoin 3,7-Diamino-2,8-dimethyl-5-phenylphenazinium Salt Sesquihydrate Safranine 0 (11.5 g, 0.033 mole) was passed through a basic anion exchange resin, Amberlite ® IRA-410 (90 ml) on a 2.5 cm × 30 cm column, activated by elution with 10% NaOH (400 ml) (ca. 1 drop/sec), with subsequent washing with water to pH of 7–8, with $H_2O$ (225 ml) (ca. 1 drop/sec) until the eluent (pH 10–11) returned to pH 8–9. The aqueous solution of the quaternary hydroxide of Safranine 0 was treated with clodanolene (11.2 g, 0.033 mole) and stored at room temperature overnight. The solid product was collected, washed with isopropanol (500 ml) at room temperature and recrystallized from ethanol to give crude material (m.p. 198°–212° dec). From the stored filtrate, more impure material was isolated. The resultant filtrate was concentrated nearly to dryness. The crystalline residue was washed with water and dried in air; m.p. 194°–197°, yield: 8.5 g (38%).

Anal. Calc'd. for $C_{34}H_{27}Cl_2N_3O_3 \cdot 1\frac{1}{2} H_2O$: C, 60.09; H, 4.45; N, 14.43. Found: C, 60.00; H, 4.64; N, 14.23.

EXAMPLE III

1-{[5-(p-Nitrophenyl)furfurylidene]amino}hydantoin 2,3-Dimethyl-1-phenyl-4-trimethylammonium-3-pyrazolin-5-one Salt Aminopyrine (46 g, 0.201 mole) was dissolved in 2-propanol (400 ml) and iodomethane (16 ml, 0.25 mole) was added. The solution was allowed to stand without heating for 24 hrs. and the resulting salt was then collected, 52 g (70%), m.p. 214°–215°.

A column of Amberlite ® IRA-410 resin (92 ml, 120 meq. minimum) was prepared by eluting with 2N sodium hydroxide solution (200 ml) and then eluting with water to neutrality. Methanol (200 ml) was then passed slowly through the column. Then the prepared quaternary salt (16.4 g, 0.044 mole) was dissolved in methanol (900 ml) and passed through the column and another 300 ml of methanol was run through. The column eluate was allowed to drip into a 2 liter erlenmeyer flask containing dantrolene (12.6 g, 0.040 mole) and the contents were occasionally swirled. After all eluate was added, the mixture was stirred well for 15 min. and then filtered. The filtrate was concentrated under reduced pressure to a dark oil which solidified upon addition of ethyl acetate (400 ml). The collected orange solid was crystallized from acetonitrile (300 ml) to yield the desired product (16.5 g, 74%), m.p. 150°-152° (resolidified and remelted at 205°-225°).

Anal. Calc'd. for $C_{28}H_{29}N_7O_6$: C, 60.10; H, 5.22; N, 17.52. Found: C, 59.91; H, 5.47; N, 17.47.

EXAMPLE IV

1-{[5-(p-Nitrophenyl)furfurylidene]amino}hydantoin 1,3-Dimethylimidazolium Salt

A. 1,3-Dimethylimidazolium iodide

A mixture of 16.4 g (0.2 mole) of 1-methylimidazole, 12.5 ml (28.4 g, 0.2 mole) of iodomethane and 600 ml of isopropanol was heated at reflux for 48 hrs. The mixture was concentrated to a volume of 300 ml and chilled. The precipitate was collected by filtration, washed with anhydrous ether and oven-dried at 60° C. to yield 37 g.

B. 1-{[5-(p-Nitrophenyl)furfurylidene]amino}hydantoin 1,3-dimethylimidazolium Salt An ion exchange column of Amberlite® IRA-410 resin (85 ml, 110 meq. on a 2.5 cm × 30 cm column) was activated by elution with 170 ml of 2N NaOH followed by washing with water to neutrality and then with 300 ml of methanol. A solution of 12.3 g (0.055 mole) of 1,3-dimethylimidazolium iodide (Part A) in 100 ml of methanol was placed on the basic anion exchange resin and eluted with methanol until the pH returned to neutral. The methanol solution of the quaternary hydroxide was collected in a flask containing 15.7 g (0.05 mole) of dantrolene suspended in 100 ml of methanol. The mixture was stirred for 60 min., then filtered. The methanol filtrate was concentrated in vacuo to dryness. The residue was triturated with 1000 ml of isopropanol and filtered, hot. The red-orange insoluble quaternary salt was then recrystallized from 100 ml of methanol, with Darco, to yield 12 g (53%), m.p. 172°-175° C.

Anal. Calc'd. for $C_{19}H_{18}N_6O_5$: C, 55.60; H, 4.42; N, 20.88. Found: C, 55.36; H, 4.42; N, 20.43.

EXAMPLE V

1-{[5-(3,4-Dichlorophenyl)furfurylidene]amino}hydantoin 2,3-Dimethyl-1-phenyl-4-trimethylammonium-3-pyrazolin-5-one Salt An ion exchange column of Amberlite® IRA-410 resin (68 ml, 88 meq. on a 2.5 cm × 30 cm column) was prepared by eluting with 180 ml of 2N NaOH then eluting with water to neutrality and finally with 350 ml of methanol. A solution of 16.4 g (0.044 m) of 2,3-dimethyl-1-phenyl-4-trimethylammonium-3-pyrazolin-5-one iodide in 800 ml of methanol was passed through the column and eluted with methanol, until the pH returned to neutral. The methanol solution of the quaternary hydroxide was collected in a flask containing a suspension of 13.5 g (0.04 mole) of clodanolene in 100 ml of methanol. Stirring was continued for 60 min. following the addition. Then the solution was filtered and the methanol filtrate concentrated in vacuo, to give 23.6 g. The crude quaternary salt was recrystallized from 2500 ml of AR acetone with Darco. The acetone filtrate was reduced to a volume of one liter and chilled. The product was collected by filtration, washed with anhydrous ether and air-dried to yield 16 g (62.3%), m.p. 191°-215° C.

A second recrystallization from acetone gave an analytical sample, m.p. 190°-215° C.

Anal. Calc'd. for $C_{28}H_{28}Cl_2N_6O_4$: C, 57.64; H, 4.84; N, 14.41. Found: C, 57.51; H, 5.01; N, 14.33.

EXAMPLE VI

1-[[[5-(4-Nitrophenyl)-2-furanyl]methylene]amino]-2,4-imidazolidinedione Choline Salt Amberlite® IRA-410 resin (110 ml, 1.3 meq/ml) was treated with 2N sodium hydroxide solution (250 ml) and washed to neutrality with water and then washed with methanol (200 ml). Choline chloride (23 g, 0.165 mole) was dissolved in methanol (100 ml) and eluted dropwise through the column with methanol. A volume of 600 ml of methanol was required to again attain neutrality of the eluate. One-third of the total eluate was added to dantrolene (16 g, 0.050 mole) in methanol (400 ml), and the solution was heated to reflux, with stirring. The hot solution was then filtered and the filtrate was concentrated to a slurry. 2-Propanol (200 ml) was added and the orange solid was collected. The solid was recrystallized from methanol (300 ml) to yield 10 g (48%). An analytical sample was obtained by recrystallization from nitromethane to m.p. 196°-198° (dec).

Anal. Calc'd. for $C_{19}H_{23}N_5O_6$: C, 54.67; H, 5.55; N, 16.78. Found: C, 54.31; H, 5.54; N, 16.78.

EXAMPLE VII

1-[[[5-(4-Nitrophenyl)-2-furanyl]methylene]amino]-2,4-imidazolidinedione 2-Methyl-2-trimethylammonium-1-propanol Salt

A. 2-Methyl-2-trimethylammonium-1-propanol iodide

A mixture containing 41.85 g (0.2 mole) of 2-amino-2-methyl-1-propanol, 50 ml (113.6 g, 0.8 mole) of iodomethane, 55.28 g of potassium carbonate and 200 ml of water was stirred for 2 hrs. at room temperature and then for 5 hrs. while heating on a steam bath. After standing overnight at room temperature, the white precipitate was collected by filtration and air-dried to yield 14.23 g, m.p. some melt 225°-227°, complete 239°-240°.

The aqueous filtrate was concentrated in vacuo to give 14.4 g.

1-[[[5-(4-Nitrophenyl)-2-furanyl]methylene]amino]-2,4-imidazolidinedione 2-Methyl-2-trimethylammonium-1-propanol Salt An ion exchange column of Amberlite® IRA-410 resin (50 ml, 65 meq. on a 2.5 cm × 30 cm column) was activated by elution with 100 ml of 2N NaOH, followed by washing with water to neutrality and then with 300 ml of methanol. A solution of 14.23 g (0.055 mole) of 2-methyl-2-trimethylammonium-1-propanol iodide (Part A) in 100 ml of methanol was placed on the basic anion exchange resin and eluted with methanol until the pH returned to neutral. The methanol solution of the quaternary hydroxide was collected in a flask containing 15.7 (0.05 mole) of dantrolene suspended in 100 ml of methanol. After stirring overnight, the mixture was filtered and the methanol filtrate concentrated in vacuo to dryness. The residue was dissolved in 150.0 ml of nitromethane, filtered hot and chilled. The quaternary salt was collected by filtration, washed with ether and air-dried to yield 13.34 g, (54.5%), m.p. melts 167°-177°, resolidified, melts 191°-194°.

An analytical sample was prepared by recrystallization from methanol, m.p. 179°-181°.

Anal. Calc'd. for $C_{21}H_{27}N_5O_6$: C, 56.62; H, 6.11; N, 15.72. Found: C, 56.21; H, 6.10; N, 15.64.

What is claimed is:
1. A compound of the formula:

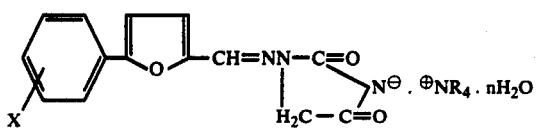

wherein X is 4-nitro or 3,4-dichloro; $^{\oplus}NR_4$ is N-methylpyridinium, 3,7-diamino-2,8-dimethyl-5-phenylphenazinium, 2,3-dimethyl-1-phenyl-4-trimethylammonium-3-pyrazoline-5-one, 1,3-dimethylimidazolium, choline, or 2-methyl-2-trimethylammonium-1-propanol; and n is 0, 0.75 or 1.5.

2. The compound 1-[[[5-(4-nitrophenyl)-2-furanyl]methylene]amino]-2,4,-imidazolidinedione N-methylpyridinium salt three quarters hydrate.

3. The compound 1-[[[5-(3,4-dichlorophenyl)-2-furanyl]methylene]amino]-2,4-imidazolidinedione 3,7-diamino-2,8-dimethyl-5-phenylphenazinium salt sesquihydrate.

4. The compound 1-[[[5-(4-nitrophenyl)-2-furanyl]methylene]amino]-2,4-imidazolidinedione 2,3-dimethyl-1-phenyl-4-trimethylammonium-3-pyrazolin-5-one salt.

5. The compound 1-[[[5-(4-nitrophenyl)-2-furanyl]methylene]amino]-2,4-imidazolidinedione 1,3-dimethylimidazolium salt.

6. The compound 1-[[[5-(3,4-dichlorophenyl)-2-furanyl]methylene]amino]-2,4-imidazolidinedione 2,3-dimethyl-1-phenyl-4-trimethylammonium-3-pyrazolin-5-one salt.

7. The compound 1-[[[5-(4-nitrophenyl)-2-furanyl]methylene]amino]-2,4-imidazolidinedione choline salt.

8. The compound 1-[[[5-(4-nitrophenyl)-2-furanyl]methylene]amino]-2,4-imidazolidinedione 2-methyl-2-trimethylammonium-1-propanol salt.

* * * * *